(12) United States Patent
Anderson et al.

(10) Patent No.: US 8,075,969 B2
(45) Date of Patent: *Dec. 13, 2011

(54) ELECTRICAL LEAD

(75) Inventors: Neil Lawrence Anderson, Roseville (AU); Evan Ka-loke Chong, South Strathfield (AU)

(73) Assignee: Cathrx Ltd, Homebush Bay, NSW (AU)

( * ) Notice: Subject to any disclaimer, the term of this patent is extended or adjusted under 35 U.S.C. 154(b) by 0 days.

This patent is subject to a terminal disclaimer.

(21) Appl. No.: 12/578,511

(22) Filed: Oct. 13, 2009

(65) Prior Publication Data

US 2010/0030308 A1   Feb. 4, 2010

Related U.S. Application Data

(60) Continuation of application No. 11/123,392, filed on May 5, 2005, now Pat. No. 7,629,015, which is a division of application No. 10/399,845, filed on Sep. 26, 2003, now Pat. No. 7,625,617, which is a continuation of application No. PCT/AU01/01339, filed on Oct. 19, 2001.

(30) Foreign Application Priority Data

Oct. 20, 2000   (AU) ...................................... PR0903

(51) Int. Cl.
B32B 1/08 (2006.01)
(52) U.S. Cl. ..................... 428/36.9; 428/34.1; 428/35.2; 428/35.3; 428/37
(58) Field of Classification Search ................ 428/34.1, 428/35.2, 35.3, 36.9, 37
See application file for complete search history.

(56) References Cited

U.S. PATENT DOCUMENTS

| | | |
|---|---|---|
| 2,002,267 A | 5/1935 | Kyle |
| 3,378,507 A | 4/1968 | Sargent et al. |
| 4,101,984 A | 7/1978 | MacGregor |
| 4,141,366 A | 2/1979 | Cross, Jr. et al. |
| 4,467,020 A | 8/1984 | Puglisi |
| 4,592,808 A | 6/1986 | Doubt |
| 4,672,970 A | 6/1987 | Uchida et al. |
| 4,734,296 A | 3/1988 | Schramm |
| 4,776,334 A | 10/1988 | Prionas |
| 4,833,568 A | 5/1989 | Berhold |

(Continued)

FOREIGN PATENT DOCUMENTS

EP   0 101 595 A1   2/1984

(Continued)

OTHER PUBLICATIONS

Supplementary European Search Report mailed on Jun. 4, 2007, for EP Application No. 01977995.8, seven pages.

(Continued)

*Primary Examiner* — Cathy Lam
(74) *Attorney, Agent, or Firm* — TraskBritt

(57) ABSTRACT

An electrically conductive member includes an elongate body, which has at least one electrically conductive region. The electrically conductive region comprises a porous polymeric material coated with an electrically conductive material. A method of manufacturing the electrically conductive member includes the steps of extruding an elongate body of polymeric material, wherein at least one region of the elongate body is porous in nature; and coating the elongate body with an electrically conductive material, such that the electrically conductive material substantially coats the pores of the at least one region.

9 Claims, 7 Drawing Sheets

U.S. PATENT DOCUMENTS

| | | | |
|---|---|---|---|
| 4,992,339 A | 2/1991 | Gerogopoulos | |
| 5,269,810 A | 12/1993 | Hull et al. | |
| 5,279,781 A | 1/1994 | Yamasaki et al. | |
| 5,330,520 A | 7/1994 | Maddison et al. | |
| 5,433,742 A | 7/1995 | Willis | |
| 5,522,874 A | 6/1996 | Gates | |
| 5,554,178 A | 9/1996 | Dahl et al. | |
| 5,609,622 A | 3/1997 | Soukup et al. | |
| 5,834,051 A | 11/1998 | Woloszko et al. | |
| 5,931,862 A | 8/1999 | Carson | |
| 6,032,061 A | 2/2000 | Koblish | |
| 6,071,278 A | 6/2000 | Panescu et al. | |
| 6,458,127 B1 | 10/2002 | Truckai et al. | |
| 6,534,581 B1 | 3/2003 | Kleyer et al. | |
| 7,178,234 B2 | 2/2007 | Kawasaki et al. | |
| 7,415,300 B2 * | 8/2008 | Anderson et al. | 600/374 |
| 7,625,617 B1 | 12/2009 | Anderson et al. | |
| 7,629,015 B2 | 12/2009 | Anderson et al. | |

FOREIGN PATENT DOCUMENTS

| | | |
|---|---|---|
| EP | 0 479 435 A2 | 4/1992 |
| EP | 0 479 435 A3 | 4/1992 |
| EP | 0 627 234 A1 | 12/1994 |
| EP | 0 778 046 A2 | 6/1997 |
| EP | 0 778 046 A3 | 6/1997 |
| EP | 0 778 046 B1 | 6/1997 |
| EP | 0 790 625 A2 | 8/1997 |
| EP | 0 790 625 A3 | 8/1997 |
| GB | 2 268 071 A | 1/1994 |
| JP | 04-044773 | 2/1992 |
| JP | 04-119113 | 4/1992 |
| JP | 07-508558 | 9/1995 |
| JP | 08-505539 | 6/1996 |
| JP | 09-219302 | 8/1997 |
| JP | 09-276240 | 10/1997 |
| JP | 04-504513 | 7/2010 |
| WO | WO-90/08466 A1 | 8/1990 |
| WO | WO-92/22687 A1 | 12/1992 |
| WO | WO-94/17852 A1 | 8/1994 |
| WO | WO-95/13844 A1 | 5/1995 |
| WO | WO-96/36860 A2 | 11/1996 |
| WO | WO-96/36860 A3 | 11/1996 |
| WO | WO-98/58681 A2 | 12/1998 |
| WO | WO-98/58681 A3 | 12/1998 |
| WO | WO-00/28894 A1 | 5/2000 |
| WO | WO-02/32497 A1 | 4/2002 |

OTHER PUBLICATIONS

Japanese Office Action for JP Application No. 2P2008-064723, dated Feb. 15, 2011, 4 pages.

International Search Report for PCT Application No. PCT/AU01/01339, dated Jan. 3, 2002.

International Preliminary Examination Report for PCT Application No. PCT/AU01/01339, dated Jun. 27, 2002.

Supplementary European Search Report mailed on Jun. 21, 2007, for EP Application No. 01977995.8, eight pages.

European Search Report mailed on Mar. 31, 2008, for EP Application No. 07024785.3, filed on Apr. 29, 2002, three pages.

Supplementary Partial European Search Report mailed Feb. 12, 2007 for EP Application No. 01977995.8, five pages.

* cited by examiner

ELECTRICAL LEAD

This application is a continuation application under 35 U.S.C. §120 of U.S. Pat. application Ser. No. 11/123,392, filed May 5, 2005, now U.S. Pat. No. 7,629,015 issued Dec. 8, 2009 which is a divisional application under 35 U.S.C. §120 of U.S. Pat. application Ser. No. 10/399,845, filed Sept. 26, 2003 (acceptance date), now U.S. Pat. 7,625,617, issued Dec. 1, 2009, which is a U.S. National Stage application under U.S.C. §371 of Internationals Application No. PCT/AU01/01339, filed Oct. 19, 2001, which claims priority to Australian Provisional Patent Application No. PR903, filed Oct. 20, 2000. Each of the foregoing disclosures is herein incorporated by reference in its entirety.

FIELD OF THE INVENTION

The present invention relates to medical electrical leads and electrodes and, in particular, to medical leads having electrodes made from a metal-coated polymeric material.

BACKGROUND ART

Electrical leads and electrodes are commonly utilized in the medical field for applications such as stimulation, sensing, ablation and defibrillation.

Traditionally, medical electrodes comprise machined metal or coiled metal wire components, which, while suitably conductive, do not provide the flexibility in both design and mechanical properties afforded by a metal-coated polymer. Furthermore, metal-coated polymers are particularly suitable for use in larger area electrodes where their lightweight, flexibility and versatility are key advantages.

The use of metal-coated or metal-filled polymers as medical electrodes has been considered. For example, in U.S. Pat. No. 5,279,781, a metal-filled fiber for use as a defibrillation electrode is described. The metal in this case is added during the spinning process. To render the electrode suitably conductive, however, requires the addition of a significant proportion of metal to the fiber, which, in turn, has an adverse effect on the mechanical strength of the electrode.

Further structures, including metal-filled silicones and intrinsically conductive polymers, have been considered for use as medical electrodes although it has been found that such structures do not have the required level of conductivity necessary for the abovementioned medical applications.

Typically, the problem encountered with using a polymeric material as an electrode is that it is difficult to obtain a good electrical connection to the electrode. In U.S. Pat. No. 5,609,622, an electrical connection was achieved by utilizing an electrode having metal wires embedded in its wall. The electrode was then subjected to an ion beam treatment with metal, such that the metal was deposited within the wall and, therefore, contacted the wires. In this case, however, the electrical connection was only shown to occur at one end of the electrode and further, it is questionable whether a good connection is achieved by this method as it relies upon the incidence of metal contacting wire through the thickness of polymeric material.

The present invention provides an electrical lead and/or electrode that overcomes the problems of the prior art.

Any discussion of documents, acts, materials, devices, articles, or the like, which has been included in the present specification, is solely for the purpose of providing a context for the present invention. It is not to be taken as an admission that any or all of these matters form part of the prior art base or were common general knowledge in the field relevant to the present invention as it existed before the priority date of each claim of this application.

DISCLOSURE OF THE INVENTION

Throughout this specification, the word "comprise," or variations such as "comprises" or "comprising, " will be understood to imply the inclusion of a stated element, integer or step, or group of elements, integers or steps, but not the exclusion of any other element, integer or step, or group of elements, integers or steps.

According to a first aspect, the present invention may include an electrically conductive member including an elongate body, the body having at least one electrically conductive region, the region comprising a porous polymeric material coated with an electrically conductive material.

Preferably, the electrically conductive member is adapted for medical use and, in particular, but not limited to, use in cardiac mapping, defibrillation or pacing, neurological applications including neural stimulation implants, muscle stimulation, sensing and ablation. Accordingly, in a preferred embodiment, the electrically conductive member may comprise part of a lead or any other form of carrier.

Typically, the electrically conductive member is an elongate tube. While the entire length of the member may be made from a porous polymer coated with an electrically conductive material, it is also envisaged that the electrically conductive member may comprise a plurality of distinct electrically conductive regions made up of the coated porous polymer.

In the embodiment wherein the electrically conductive member is tubular, it is preferred that the pores of the at least one electrically conductive region are present substantially across the diameter of a sidewall of the tubular structure. Accordingly, in this embodiment, electrical connection may be made from internal a lumen of the tube. It is further envisaged that electrical connection may be made from within the sidewall of the tube as further discussed below.

Rather than a tube, the electrically conductive member may comprise a solid cylindrical member. In this embodiment, it is again preferred that the pores of the at least one electrically conductive region are present substantially across the diameter of the cylindrical member.

In a preferred embodiment, the pores of the polymeric material of the at least one electrically conductive region are greater than 5 microns and preferably between 30 microns and 100 microns. When the porous polymeric material is coated with an electrically conductive material, the electrically conductive material preferably coats and lines at least some of, and preferably all of, the pores.

Typically, the electrically conductive material is a metal and, preferably, a biocompatible metal such as platinum. It is envisaged, however, that a combination of two or more metals or metal alloys may be used to improve electrical conductivity. For example, it may be desirable to provide a first layer of copper or silver or any other suitably conductive metal and a second layer of platinum to enable use of the electrically conductive member within a body.

The coating of the porous polymeric material preferably creates a suitably thick layer of metal coating across the at least one electrically conductive region. Preferably, the resistance of the coating is less than 100 ohms and more preferably less than 10 ohms.

The porous polymeric material may be expanded polytetrafluoroethylene (PTFE), wherein the pore size is adjusted to allow the metal coating to penetrate the pores and to produce a coating of sufficient thickness to provide adequate electrical conductivity. Other materials are envisaged including, but not limited to, porous silicones, porous polyurethanes, polyether block amide (PEBAX) or nylon. In each case, the pore size may be varied depending upon the method of formation of the porous material or by the addition of additives such as sodium chloride (NaCl), sodium bicarbonate ($Na_2HCO_3$) or polyglycolide, which can be leached out following molding or extrusion, leaving a porous structure.

Alternatively, the pores of the polymeric material may be formed by drilling into the polymer using a laser drill. This has the particular advantage of enabling only a portion of the polymer to be of a porous nature.

The at least one electrically conductive region may be electrically connected to an electrical conductor.

In one embodiment, the electrical conductor is a straight or coiled wire, or number of wires, embedded within the body of the electrically conductive member and preferably within the at least one electrically conductive region of the member. If the electrically conductive member is a solid cylindrical member, the wire or wires may be coiled in a helical manner within the at least one electrically conductive region. If the electrically conductive member is a tubular structure, the wire or wires may be coiled in a helical manner within the wall of the tube and preferably within the at least one electrically conductive region. In either embodiment, the wire(s) may extend through several pores of the at least one electrically conductive region. Accordingly, when the porous polymeric material of the at least one region is coated with the electrically conductive material, the portions of wire that extend through the pores may be simultaneously coated with the electrically conductive material, thereby creating a good electrical connection between the electrical conductor and the electrically conductive region.

The wires may be single wires or multifilament wires. Further, the wire or wires may be made of copper, preferably coated with a noble metal, such as palladium or platinum, for corrosion resistance. Alternatively, the individual wires may be a multifilament stainless steel wire. Other suitable materials include, but are not limited to, platinum or platinum alloy, MP35N or ELGILOY®.

In the above embodiment, depending upon the application of the electrically conductive member, the wire(s) may be connected by an insulated conductor to either a source of electricity or to an analyzer means. Typically, the wire(s) are connected to the insulated conductor by way of welding. Alternatively, they may be connected by electrically conductive adhesives or by soldering.

In a further embodiment, the electrical conductor is located internal the elongate body of the electrically conductive member. For example, if the electrically conductive member is a tube having at least one electrically conductive region, the electrical conductor may be positioned within the lumen of the tube. In this embodiment, the electrical conductor is preferably adapted such that it engages the internal surface of the tube. To ensure that the electrical conductor engages the tube, it is preferred that the electrical conductor comprises a resilient spring, such as a spiral spring, that, once positioned in the tube, can expand into contact with the inner wall of the tube.

In another embodiment, the electrical conductor may be a spring formed from a shape memory alloy such as Nitinol. The shape memory spring preferably moves, when exposed to a pre-determined temperature, from a first position to a second position, wherein, when in the second position, the spring expands such that it has an outer diameter greater than the inner diameter of the tube. Accordingly, when internal the lumen of the tube and when in the expanded second position, the spring engages the inner surface of the tube to a sufficient extent to provide a good electrical connection between the electrical conductor and the at least one electrically conductive region.

In one embodiment, the shape memory alloy spring expands into contact with the inner surface of the tube upon exposure to body temperature.

The shape memory spring may be connected to an insulated conductor by welding, the use of electrically conductive adhesives or soldering.

In the above embodiments, it is preferred that the electrical conductor such as the wire(s) embedded within the electrically conductive member or a shape memory alloy spring positioned within a lumen of a tubular electrically conductive member, extends the entire length of the electrically conductive member, or at least the length of the at least one electrically conductive region, such that a good electrical connection between the electrical conductor and the at least one electrically conductive region can be made.

In another embodiment, the electrical conductor is adapted to engage an end of the electrically conductive member. For example, the electrical conductor may include a shape memory alloy tube that is adapted to expand and increase its internal diameter upon heating above a pre-determined temperature or exposure to a particular pre-determined temperature. The shape memory alloy tube may then be slid over an end of the electrically conductive member. Upon heating above or cooling below the pre-determined temperature depending on the type of shape memory alloy, the shape memory alloy tube preferably returns to its original unexpanded shape, therefore, effectively clamping down on an end of the electrically conductive member. This embodiment provides a uniform radial pressure on the end of the member and provides a good electrical connection between the electrical conductor and the at least one electrically conductive region of the member. If the electrically conductive member is a tube, it may be necessary to provide an inner tube which is relatively stiff and which may be positioned internal the lumen of the tube to prevent collapse of the member.

In a second aspect, the present invention may include a method of manufacturing the electrically conductive member of the first aspect, the method comprising the steps of:

(i) extruding an elongate body of polymeric material, wherein at least one region of the elongate body is porous in nature; and (ii) coating the elongate body with an electrically conductive material such that the electrically conductive material substantially coats the pores of the at least one region.

While the entire length of the elongate body may be coated with the electrically conductive material, in the embodiment wherein there are distinct regions of porous polymeric material, it may be preferred that only the distinct porous regions are coated with the electrically conductive material rather than the entire length of the elongate body, which may include non-porous regions.

Where the electrical conductor comprises a straight or coiled wire, the electrically conductive member may be manufactured in a number of stages. For example, a first tube, or layer, or solid cylindrical member may be formed from either a porous polymeric material or non-porous polymeric material or a combination thereof. The wire may then be wrapped around and along at least a portion of the first tube or solid cylindrical member in a helical manner or extended along at least a portion of the length of the first tube or layer or solid cylindrical member. The wire and the first tube or layer or solid cylindrical member may then be overlaid with a coating or another layer. The coating or the other layer may be a porous polymeric material or, alternatively, a polymeric material having regions that are of a porous nature. In one embodiment, the coating may be a second tube.

In a further embodiment of the second aspect, the electrically conductive member may comprise a tube. In this embodiment, the electrical conductor is positioned within the lumen of the tube. The electrical conductor is preferably positioned such that it engages the internal surface of the tube. To ensure that the electrical conductor engages the tube, it is preferred that the electrical conductor comprises a resilient spring, such as a spiral spring that, once positioned in the tube, can expand into contact with the inner wall of the tube.

In another embodiment of the second aspect, the electrical conductor can be formed in a spring form from a shape memory alloy such as Nitinol. The shape memory spring can preferably move from a first position to a second position, wherein, when in the second position, the spring could expand such that it had an outer diameter greater than the inner diameter of the tube.

The electrical conductor may be adapted to engage an end of the electrically conductive member. For example, the electrical conductor may include a shape memory alloy tube that is adapted to expand and increase its internal diameter upon heating above a pre-determined temperature. The shape memory alloy tube may then be slid over an end of the electrically conductive member. Upon heating above or cooling below the pre-determined temperature depending on the type of shape memory alloy, the shape memory alloy tube preferably returns to its original unexpanded shape, therefore effectively clamping down on an end of the electrically conductive member. This embodiment provides a uniform radial pressure on the end of the electrically conductive member and provides a good electrical connection between the electrical conductor and the at least one electrically conductive region of the member.

Typically, the electrically conductive material is applied to the elongate body or preferably to the at least one electrically conductive region using a wet technique such as electroless plating. In this embodiment, the electrically conductive material may be forced through the pores of the at least one electrically conductive region by the application of pressure.

Alternatively, the electrically conductive material may be applied by electroless plating followed by the additional step of electroplating.

Each of the above processes preferably ensures that a coating of electrically conductive material penetrates substantially all the pores of the electrode. If the at least one region of electrically conductive material has pores disposed substantially throughout the entire thickness of the region, it is envisaged that electrical connection may be made by way of an electrical conductor, as described above, either within the wall of the elongate body or on the inside of the elongate body (for example, if the elongate body is a tubular structure).

The process of coating the elongate body with an electrically conductive material such that the pores of the at least one electrically conductive region are coated with such a material may involve a number of steps prior to the actual coating with the electrically conductive material. The steps include:
 (1) Cleaning.
 (2) Surface Modification.
 (3) Catalysis.
 (4) Coating.
(1) The material to be coated is typically washed in an organic solvent, such as acetone or ethyl acetate, or in a solution containing a suitable surface active agent. Usually some agitation is required, such as from an ultrasonic cleaner or a shaker water bath. The step of cleaning may be carried out above room temperature.

(2) The step of surface modification results in a more wettable or hydrophilic surface, such that the deposition of the coating may be accelerated and, further, chemical and mechanical adhesion of the coating to the surface may be improved.

Chemical adhesion may be improved by creating the most suitable functional groups on the surface of the polymer such as amides, while mechanical adhesion may be improved by creating a roughened surface using chemical (etching) or mechanical (sandblasting) methods.

Typically, the surface modification chemicals are infused into the pores using pressure via a pump or syringe. Alternatively, the porous material to be coated may be placed in the treatment solution and evacuated in a vacuum, thereby removing gas bubbles from within the porous structure resulting in contact of all surfaces with the treatment solution.

Additionally, plasma treatment may be used to improve wettability and/or improve chemical or mechanical adhesion.

Following this step, the structure to be coated is rinsed several times, preferably in deionized water.
(3) The catalyst step results in the deposition of a small amount of noble metal on the surface of the material. This provides the sites for deposition of the coating material, for example, platinum. While typical electroless plating uses a tin/palladium catalyst, it is preferred that a process that eliminates the tin is used. For example, palladium in an acidic aqueous solution or dimethyl sulfoxide, both of which can be reduced in a hydrazine solution, is preferred. The latter is particularly useful as, being an organic solution, it allows improved wettability for many substrates.

In one embodiment of the catalysis of a material such as silicone, the catalyst, in the form of palladium metal powder, can be mixed into a silicone dispersed in a solvent and then infused into the pores and cured prior to coating. In this embodiment, a small concentration of actual silicone is required so as to provide a thin layer on the surface of the pores rather than fill the pores with silicone. The palladium metal will act as a catalyst and will be bound to the silicone and, therefore, increase the adhesion of the coating material that is subsequently applied.

Alternatively, the silicone mix may be infused with palladium prior to molding or extrusion.

The catalyst step may be performed a number of times.
(4) The coating process preferably uses electroless plating, wherein a number of metals may be deposited using either commercially available or custom made solutions of complex metal ions, together with a stabilizer and an added reducer. The solution typically allows controlled deposition of a metal over a specific period of time. If a biocompatible electrode is required, it is preferred that the metal is platinum.

A fifth step may be added to the above process if a thicker coating of metal and, therefore, higher conductivity is required. This would involve further electroless plating or electroplating.

In a further embodiment, following the process of coating, the pores are infused with a liquid adhesive such as, but not limited to, a silicone dispersant to effectively seal the pores. Preferably, the infusion of the adhesive is carried out from within the electrically conductive member when the member is a tubular structure. This embodiment has the advantage of enabling an electrically conductive member to be implanted in a body for long periods of time with minimal tissue ingrowth into the member. This facilitates easy removal of the member if required.

In a third aspect, the present invention may include an electrically conductive member including an elongate body, the elongate body having at least one electrically conductive region comprising a polymeric material, together with at least one electrical conductor wherein at least a portion of the polymeric material and at least a portion of the at least one electrical conductor have a coating thereon of an electrically conductive material.

Preferably, the elongate body comprises a tubular body made of a suitable polymer material. The electrical conductor is preferably housed within at least part of a side wall of the tubular body. In addition to being housed within a side wall of the tubular body at the at least one electrically conductive region of the body, the electrical conductor may extend along the entire length of the tubular body.

The elongate body preferably comprises a first cylindrical inner member and a second outer member, the second outer member substantially forming a coating around the first inner member. The second outer member preferably extends over the entire length of the first inner member. The at least one electrical conductor is preferably sandwiched between the first inner member and the second outer member.

The first inner member may be made from a suitable polymeric material such as polyurethane, polyether block amide (PEBAX), PEEK or polyimide. The second outer member is preferably formed from a similar polymeric material to that of the first inner member. Further, it is preferred that the second outer member is made from a transparent, or at least substantially transparent, material such that the at least one electrical conductor may be viewed through the second outer member.

Preferably, the second outer member is much thinner than the first inner member and typically, the second outer member is sufficiently thick to only just cover the at least one electrical conductor.

The at least one electrical conductor may comprise a metal wire or wires made from material such as PFA, polyimide insulated copper wire(s) or copper alloy wire(s). Preferably, the wire(s) have a diameter of approximately 0.025 mm to 0.3 mm.

Typically, during manufacture, single wires may be wound substantially around the circumference of the first inner member. Preferably, between 8 to 24 wires are wound around the first inner member in this manner, wherein each wire has a predetermined spacing between it and the next wire. These 8 to 24 wires may form a particular group that is spaced from a second or subsequent group of wires by a gap, which is preferably larger than the gap between each wire of each group. In this way, identification of each group may be more easily determined. To aid identification, each group may further be color coded.

The at least one electrical conductor may be helically wound around the first inner member. However, the present invention is not limited to the particular arrangement of the at least one electrical conductor and a number of combinations and orientations are envisaged.

Preferably, at least one portion of the at least one electrical conductor is not overlaid by the second outer member, that is, the at least one portion is exposed to the outside environment. The at least one portion of the electrical conductor of this embodiment is preferably coated with the electrically conductive material. It is further preferred that at least a portion of the polymeric elongate body adjacent the exposed portion of the electrical conductor is also coated with the electrically conductive material.

Typically, a band around the circumference of the elongate body is coated, together with the exposed portion of the electrical conductor, to form a band electrode on the elongate body.

Preferably, the electrically conductive material is a metal and, preferably, a biocompatible metal such as platinum. It is envisaged that a combination of two or more metals or metal alloys may be used, however, to improve electrical conductivity. For example, it may be desirable to provide a first layer of copper or silver or any other suitably conductive metal and a second layer of platinum to enable use of the electrically conductive member within a body.

It is preferred that the exposed at least one portion of the electrical conductor is protected from corrosion. This may be achieved by, for example, immersing the elongate body in a solution such as palladium chloride, which will coat the exposed portion(s).

In a fourth aspect, the present invention provides a method of manufacturing an electrically conductive member, the method comprising the steps of:

(i) extruding an elongate inner member from a polymeric material;

(ii) applying at least one electrical conductor to an exposed surface of the inner member;

(iii) overlaying the inner member and the at least one electrical conductor with an outer member made from a polymeric material, such that the at least one electrical conductor is covered by the outer member;

(iv) exposing at least a portion of the at least one electrical conductor; and (v) coating the exposed portion of the at least one electrical conductor and at least a portion of the outer member with an electrically conductive material.

Preferably, the inner member is extruded as a tube made from a suitable material such as polyurethane or polyether block amide (PEBAX).

The at least one portion of the at least one electrical conductor may be exposed by a number of means including, but not limited to, applying heat, chemicals or lasers to remove the area of the outer layer covering the at least one portion. Desirably, a laser technique is used (e.g., quadruple Yag laser) as such a technique provides good accuracy. For example, the laser beam is capable of following a particular path of, say, a helically wound wire acting as the at least one electrical conductor. While only a small portion of the at least one electrical conductor may be exposed in this manner, the present invention is not limited to the amount of electrical conductor exposed and, indeed, the entire electrical conductor may be exposed.

For high energy applications, such as radio frequency (RF) or microwave ablation, adjacent electrical conductors may be exposed and coated with electrically conductive material to form a single electrode. Such a configuration decreases the current density. The electrical conductors of this embodiment may be electrically connected to each other at a proximal end of each electrical conductor. The number of electrodes formed together with the spacing between each electrode may be varied.

The exposed portion of electrical conductor(s) may be protected from corrosion by immersion in an acidic solution of, for example, palladium chloride, which will coat all the exposed portions.

It is desirable that the at least one portion of the at least one electrical conductor and at least a portion of the elongate body, which together are coated to form an electrode, are catalyzed. To prevent catalysis of the remainder of the elongate body or electrical conductor that form a non-electrode area, these areas are protected from catalysis by masking them by, for example, photolithography or by using pieces of heat shrink tubing such as PET to protect the areas. An alternative to masking is the use of an ink that is pad printed over the areas to be coated and, thus, the areas that are to become the electrodes. The ink used may or may not be electrically conductive but, in any event, should be able to catalyze a subsequent plating step. If radio opacity is required, it may be desirable to use an ink including colloidal palladium or silver.

The catalyst step results in the deposition of a small amount of noble metal on the surface of the material to be coated. This provides the sites for deposition of the electrically conductive material, for example, platinum. While typical electroless plating uses a tin/palladium catalyst, it is preferred that a process that eliminates the tin is used. For example, palladium in an acidic aqueous solution or dimethyl sulfoxide, both of which can be reduced in a hydrazine solution, is preferred. The latter is particularly useful as, being an organic solution, it allows improved wettability for many substrates.

The catalyst step may be performed a number of times.

The coating process preferably uses electroless plating, wherein a number of metals may be deposited using either commercially available or custom made solutions of complex metal ions, together with a stabilizer and an added reducer. The solution typically allows controlled deposition of a metal over a specific period of time. If a biocompatible electrode is required, it is preferred that the metal is platinum.

If relatively thick coatings are required, it is preferred that a porous polymer is used.

The electrodes formed with respect to the third and fourth embodiments may be protected by a layer of, for example, polyethylene glycol or mannitol. Such a protective layer preferably allows an electrical charge to pass therethrough.

The following examples describe the preparation of the electrode according to several embodiments of the first and second aspects of the present invention.

EXAMPLE 1

A porous polyurethane tube was made using a spraying system. First, a wire mandrel was connected to an electrical motor using a chuck. The wire was simultaneously coated with a mixture of polyurethane (PELLETHANE®) dissolved in dimethylformamide (1% polyurethane) and water. The water polymerized the polyurethane prior to deposition, creating a porous layer. A copper wire was then wound onto the coated mandrel and a further layer was uniformly coated with the mixture of polyurethane dissolved in dimethylformamide and water. The spraying continued until the appropriate diameter was achieved, i.e., 2.2 mm (this was chosen as once assembled into a lead, a 2.2 mm lead body would comfortably pass down a 7 French introducer).

The porous component was then coated with platinum using the normal cleaning, surface modification, catalysis and coating steps previously outlined.

The resistance was then measured to be approximately $0.5\Omega$ for a 1 cm length of the porous component, and approximately $1\Omega$ from the end of the copper wire to the surface of the component.

EXAMPLE 2

An expanded PTFE tube was supplied by Impra, which had a pore size of 30 microns. The tube was immersed in alcohol and placed in an ultrasonic cleaner to remove air bubbles and wet the surface.

The sample was removed from the alcohol and etched for 1 minute with FLUOROETCH® from Acton Technologies, Inc., Pittson, PA. A syringe was used to try and force the solution through the pores; however, this was unsuccessful.

The tube was then catalyzed using a 2 g/l solution of $PdCl_2$ in Dimethyl Sulfoxide for 5 minutes, intermittently attempting to force the solutions through the pores. This was followed by a reduction step in 4% Hydrazine solution.

The catalyzed tube was then electrolessly coated using a platinum complex solution and hydrazine.

After 1.5 hours, the sample was a shiny, metallic color on the outside.

After drying, the resistance along the surface was found to be approximately $20\Omega$ for a 1 cm length; however, the resistance through the thickness varied from $25-50\Omega$.

EXAMPLE 3

Another expanded PTFE tube was supplied by Impra; however, this time, the pore size was increased to 90 microns. The tube was immersed in alcohol and placed in an ultrasonic cleaner to remove air bubbles and wet the surface.

The sample was removed from the alcohol and etched for 30 seconds with FLUOROETCH® from Acton Technologies, Inc., Pittson, PA. A syringe was used to try and force the solution through the pores. This time, the solution was able to freely pass through the structure.

The tube was then catalyzed using a 2 g/l solution of $PdCl_2$ in Dimethyl Sulfoxide for 5 minutes, intermittently forcing the solutions through the pores. This was followed by a reduction step in 4% Hydrazine solution.

The catalyzed tube was then electrolessly coated using a platinum complex solution and hydrazine, intermittently forcing the solution through the pores.

After 1.5 hours, the sample was a shiny, metallic color on the outside.

After drying, the resistance along the surface was found to be approximately $1.5\Omega$ for a 1 cm length. The resistance through the thickness was approximately $1.5\Omega$. No materials were removed using a standard tape test to measure adhesion.

A 4 mm length was then cut and a 2.1 mm diameter Nitinol spring (from Microvena, White Bear Lake, Minnesota, USA) was straightened and passed up the middle of the cut platinum-coated tube. The structure was then placed in the oven at 70° C. and the Nitinol spring went back to its original shape clamping on the inside of the platinum-coated tube.

A length of 0.2 mm diameter copper wire was then welded to one end of the Nitinol spring. The resistance was found to be 1.8 ohms from the end of the copper wire and the outside of the platinum-coated expanded TEFLON®.

A PEBAX tube was passed over each end of the spring and then glued with epoxy forming a butt joint on each side of the platinum-coated expanded TEFLON® component.

After curing, the lead was then tested in an isolated cow heart, by immersing the heart with an electrode attached into a conductive media and RF energy passed through the electrode to the heart, creating lesions. The test device produced similar lesions to a commercially available ablation lead.

The same lead was tested when delivering pacing pulses and a suitable impedance resulted.

Due to flexibility and versatility, the electrodes can be made different shapes, sizes, numbers and spacing. This is important when designing new leads for various applications, e.g., ablation leads for treating atrial fibrillation.

The following examples describe the preparation of the electrode according to several embodiments of the third and fourth aspects of the present invention.

EXAMPLE 4

A 1.6 mm diameter cable was sourced from MicroHelix, Inc., Portland, Oregon. The cable contained eight insulated wire coils in the wall of the tube. The insulating layer was made from a thin layer of PEBAX. Over one of the wires, a 4 mm length of insulation was removed to expose the corresponding amount of wire. A 4 mm band of the cable around the exposed wire was masked. Some plateable conductive ink from Creative Materials Tyngsboro, MA was coated around the unmasked region covering the exposed conductor. The electrode with ink was then immersed in a platinum complex electroless bath and coated for 1 hour at 60° C. using Hydrazine as the reducer resulting in a thickness of 0.5 micron. The pacing impedance of the plated electrode was then measured in a 0.18% NaCl solution using a nickel plate as the return electrode. The pacing pulse used was 5 volts for 0.5 ms. The impedance was found to be 250 ohms. This value was compared to a commercially available ablation electrode, which was found to be 180 ohms. No damage to the coated electrode resulted.

EXAMPLE 5

A 1.6 mm diameter cable was sourced from MicroHelix, Inc., Portland, Oregon. The cable contained eight insulated wire coils in the wall of the tube. The insulating layer was a thin layer of PEBAX. Over one of the wires, a 4 mm length of insulation was removed to expose the corresponding amount of wire. A 4 mm band of the cable around the exposed wire was masked. Some plateable conductive ink (CMI 117-31) from Creative Materials Inc., Tyngsboro MA was coated around the unmasked region covering the exposed conductor. The electrode ink was coated with a 3 micron layer of copper using electroless plating. The copper-coated electrode was then immersed in an acid palladium chloride solution to catalyze the surface and immersed again in platinum complex electroless bath and coated for 1 hour at 60° C. using Hydrazine as the reducer. The pacing impedance of the plated electrode was then measured in a 0.18% NaCl solution using a nickel plate as the return electrode. The pacing pulse used was 5 volts for 0.5 ms. The impedance was found to be 120 ohms. This value was compared to a commercially available ablation electrode, which was measured to be 180 ohms. No damage to the coated electrode resulted.

EXAMPLE 6

A 1.6 mm diameter cable was sourced from MicroHelix, Inc., Portland, Oregon. The cable contained eight insulated wire coils in the wall of the tube. The insulating layer was a thin layer of PEBAX. Over one of the wires, a 4 mm length of insulation was removed to expose the corresponding amount of wire. A 4 mm band of the cable around the exposed wire was masked. Some plateable conductive ink (CMI 117-31) from Creative Materials, Inc., Tyngsboro MA was coated around the unmasked region covering the exposed conductor. The electrode ink was coated with a 3 micron layer of copper using electroless plating. The copper-coated electrode was then immersed in an acid palladium chloride solution to catalyze the surface and immersed again in platinum complex electroless bath and coated for 1 hour at 60° C. using Hydrazine as the reducer.

The electrode was then placed on a piece of meat immersed in a 0.18% solution of NaCl and a stainless steel return electrode underneath. High-frequency RF power was delivered through the electrode for 60 seconds, resulting in a lesion similar to a commercially available ablation electrode.

EXAMPLE 7

A 1.6 mm diameter cable was sourced from MicroHelix, Inc., Portland, Oregon. The cable contained eight insulated wire coils in the wall of the tube. The insulating layer was a thin layer of PEBAX. Over one of the wires, a 4 mm length of insulation was removed to expose the corresponding amount of wire. A 4 mm band of the cable around the exposed wire was masked. Some plateable conductive ink (CMI 117-31) from Creative Materials, Tyngsboro, MA was coated around the unmasked region covering the exposed conductor. The electrode ink was coated with a 3-micron layer of copper using electroless plating. The copper-coated electrode was then immersed in an acid palladium chloride solution to catalyze the surface and immersed again in platinum complex electroless bath and coated for 1 hour at 60° C. using Hydrazine as the reducer.

The coated electrode was then immersed in a 0.18% NaCl solution using a nickel plate as the return electrode. A biphasic defibrillation pulse 130 volts in amplitude and 6 ms in pulse width was delivered through the coated electrode, which resulted in no damage to the electrode and an impedance of 130 ohms.

BRIEF DESCRIPTION OF THE DRAWINGS

Preferred embodiments of the invention are now described with reference to the accompanying drawings, in which.

DETAILED DESCRIPTION

Figure 1A:
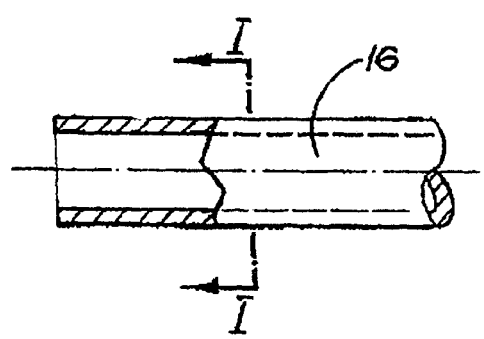
FIGS. 1a, 1b, and 1c are side elevational views illustrating a construction of one embodiment of the present invention.

The lead 10 of the present invention includes an elongate body 11 having at least one electrically conductive region 20 thereof made from a porous polymeric material. The porous polymeric material is coated with an electrically conductive material and preferably a metal such as platinum.

As discussed above, the lead 10 of the present invention is adapted for medical use and, in particular, use in cardiac mapping, defibrillation or pacing, neurological applications including neural stimulation implants, muscle stimulation, sensing and ablation.

As depicted in the drawings, the lead 10 has a tubular structure having a wall 12 and an internal lumen 13. While only one region 20 of the tube may be made from the porous polymeric material, it may be preferable that the entire length of the tube is made from the material.

The pores within the wall 12 are preferably greater than 5 microns and preferably between 30 microns and 100 microns.

The coating of the porous polymeric material with the metal creates a suitably thick layer of metal coating, thereby increasing electrical conductivity through the lead 10.

To establish a good electrical connection, the lead 10 includes a conductive member 14.

Figure 1B:
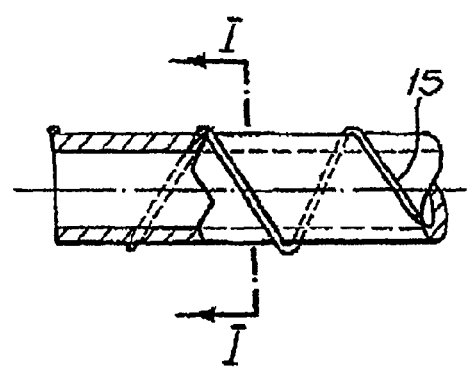
Figure 2B:
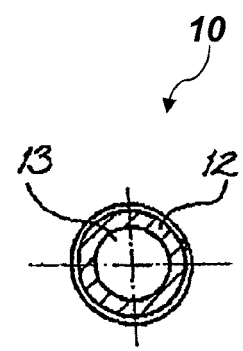
Figure 1C:
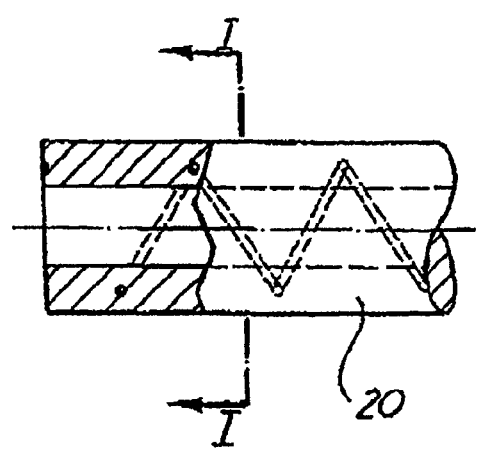
Figure 2C:
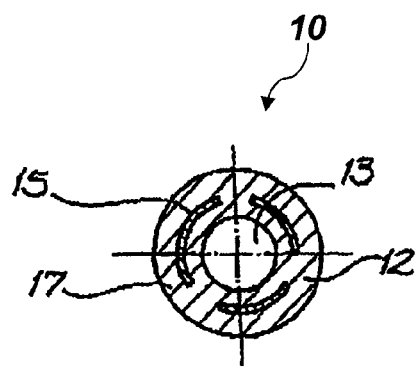

In one embodiment, depicted in FIGS. 1a, 1b, 1c, the conductive member 14 comprises a coiled wire 15 embedded within a wall 12 of the lead 10(FIG. 21). The wire 15 is wrapped around and along a substantial length of the lead 10 and preferably along the entire lead. While not shown, the wire 15 may pass through several pores of the polymeric material and, thus, when the porous polymer is coated with the metal, the portions of wire 15 within the pores may simultaneously be coated with the metal, thereby creating a good electrical connection between the wire and the at least one electrically conductive region 20.

Figure 3:
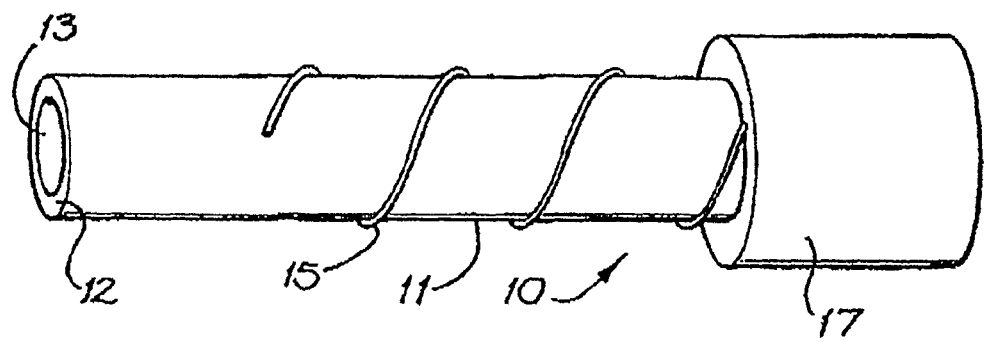
FIG. 3 is a side elevational view of a cut-away portion of an embodiment of the invention.

As shown in FIGS. 1a, 1b and 1c, the lead of this embodiment may be made in a number of stages. A first tube 16 is created as shown in FIG. 1a. The first tube 16 may, or may not be, porous in nature. The wire 15 is subsequently wrapped around and along the first tube 16 in a helical manner and the wire 15 and first tube 16 subsequently overlayed with a second porous polymer material 17(FIG. 3).

Figure 4A:
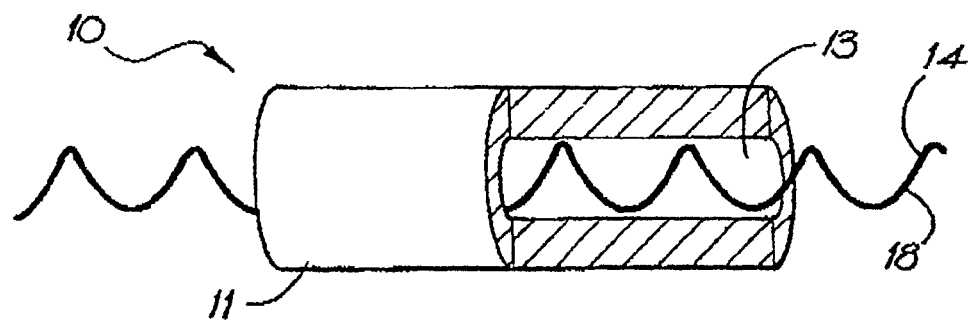
FIGS. 4a and 4b are part cut-away, part side elevational views of a further embodiment of the invention.
Figure 4B:
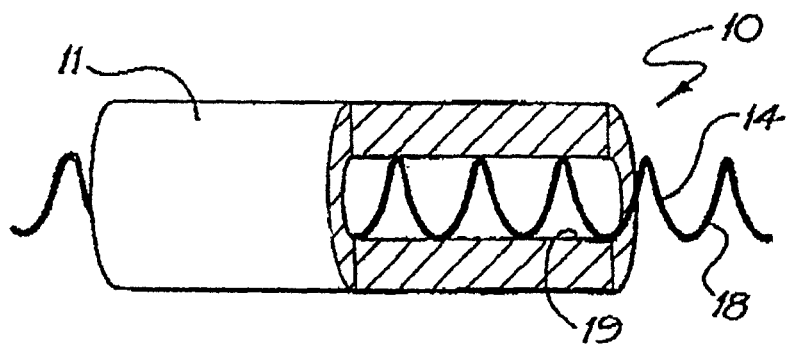

In another embodiment, the conductive member 14 is a shape memory alloy spring 18(FIGS. 41 and 4b) such as a Nitinol spring. The spring 18 of this embodiment is positioned internal the lumen 13 of the lead 10. In use, the spring 18 may be exposed to a pre-determined temperature that causes it to expand such that it abuts with the internal surface 19 of the lead 10. Preferably, the spring 18 can normally expand to such an extent that its external diameter is greater than the diameter of the lumen 13 resulting in a good electrical connection between the spring and the at least one electrically conductive region.

Figure 5A:
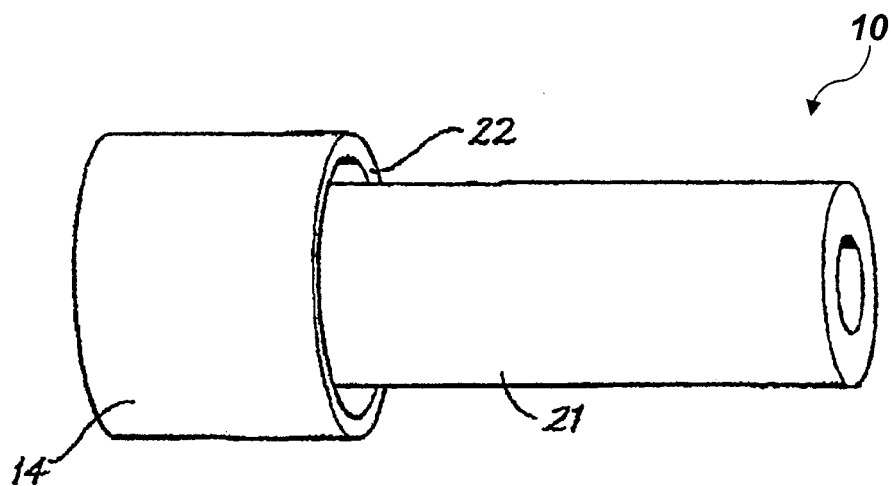
FIGS. 5a and 5b are side elevational views of a further embodiment of the invention.
Figure 5B:
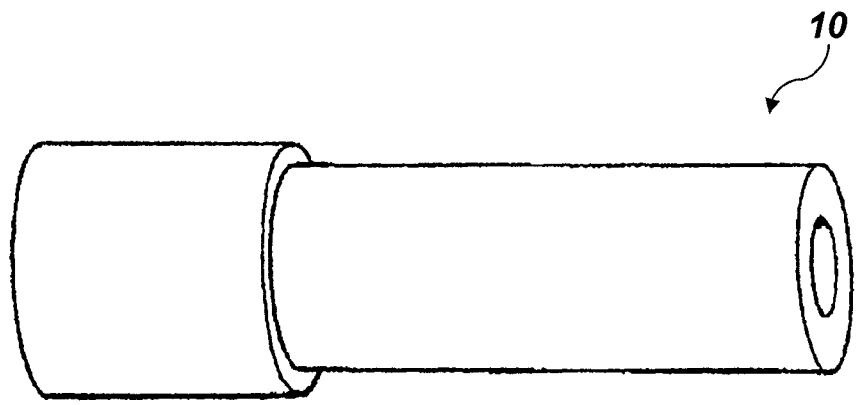

In another embodiment of the invention depicted in FIGS. 5a and 5b, the conductive member 14 is adapted to engage one end 21 of the lead 10. Preferably, the conductive member is a shape memory alloy tube 22, which is adapted to expand and increase its internal diameter upon heating above or cooling below a pre-determined temperature depending on the type of shape memory alloy. The shape memory alloy tube 22 may then be slid over the end 21 of the lead 10. Upon heating up or cooling below the pre-determined temperature depending on the type of shape memory alloy, the shape memory alloy tube 22 returns to its original unexpanded shape, therefore, effectively clamping down on an end of the lead 10 as shown in FIG. 5b. Accordingly, there is provided a uniform radial pressure on the end 21 of the lead 10, which results in a good electrical connection between the shape memory alloy tube 22 and the at least one electrically conductive region. In this embodiment, it may be necessary to provide an inner, relatively stiff tube (not shown), which may be positioned internal the electrode 10 to prevent collapse of the lead 10.

Once the lead 10 has been coated with the selected metal, the lead 10 may be cut to the desired length depending on the application of the electrode. For example, a defibrillation electrode formed from the lead may need to be a length of around 60 mm, whereas a lead acting as an electrode for mapping or sensing need only be a few millimeters in length.

Figure 6:
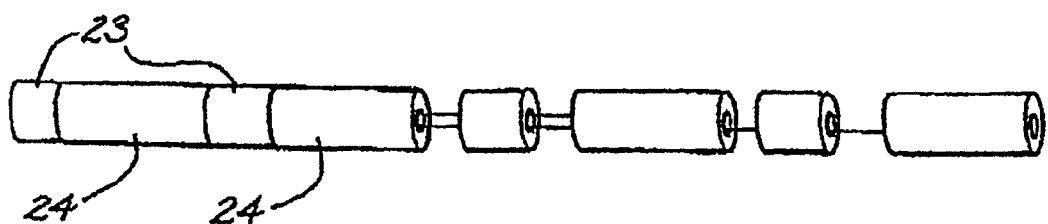
FIG. 6 is a schematic view of a multi-electrode assembly incorporating electrically conductive regions of the present invention.
Figure 7:
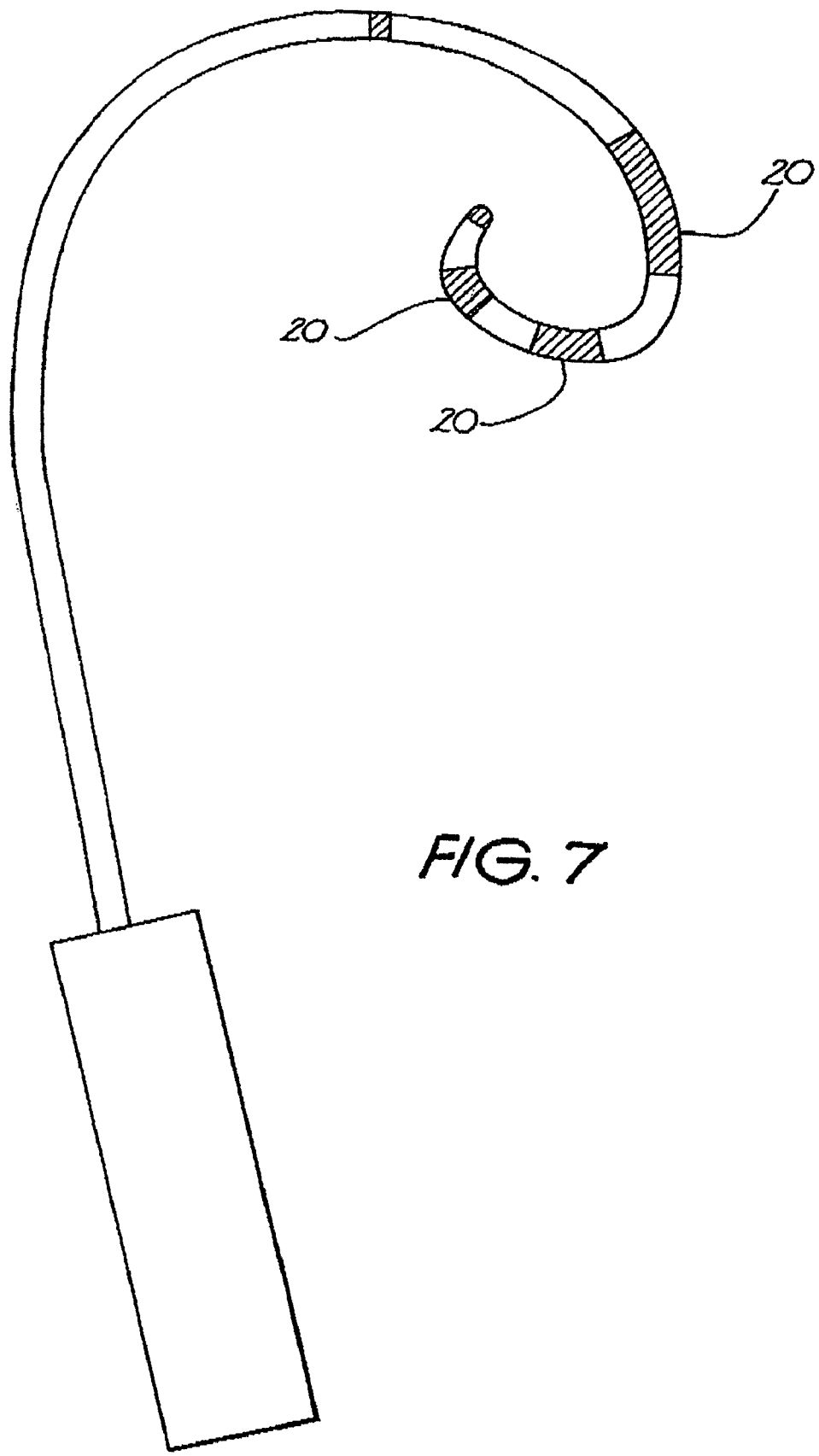
FIG. 7 is a perspective view of a number of electrically conductive regions of the present invention in an electrode assembly.

A multi-electrode system along a lead may be constructed by threading together lengths of coated tubes 23 or uncoated tubes 24 of specified lengths as depicted in FIG. 6. The coated tubes 23 and uncoated tubes 24 are joined together using butt joints, which may have spring or tubing supports (not shown) within the lumen of the respective coated and uncoated tubes 23 or 24.

Figure 8A:
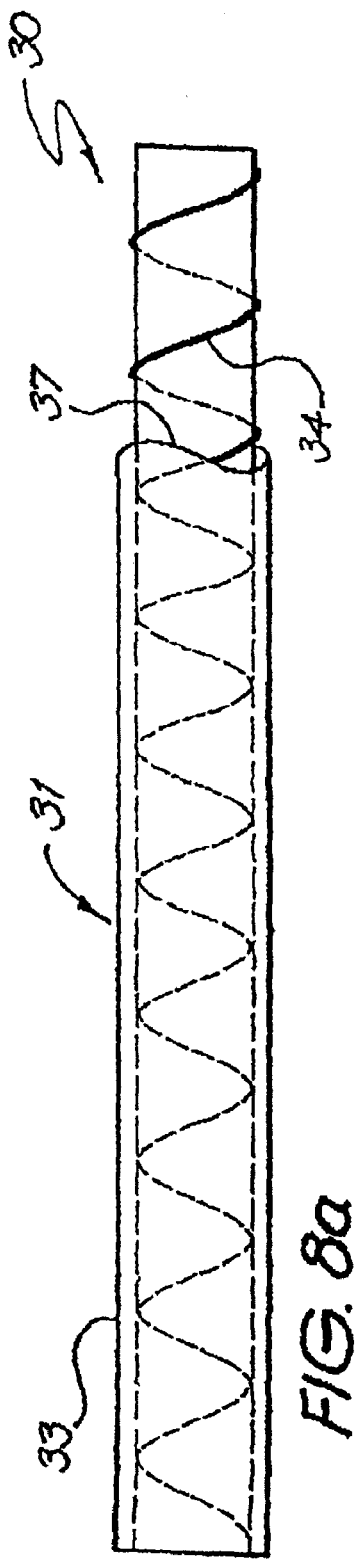
FIGS. 8a, 8b, and 8c are schematic views showing the steps of manufacture of an electrically conductive member according to a further aspect of the invention.
Figure 8B:
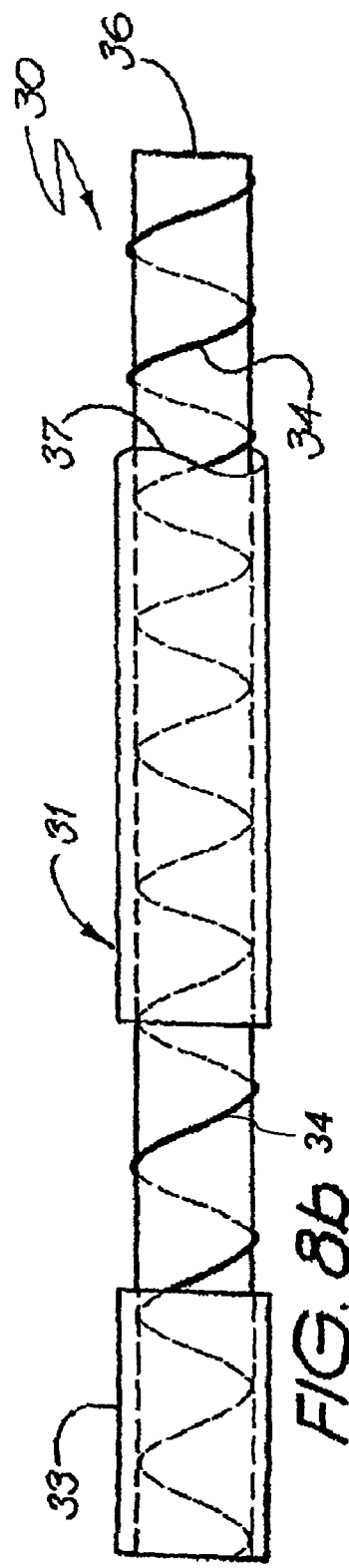
Figure 8C:
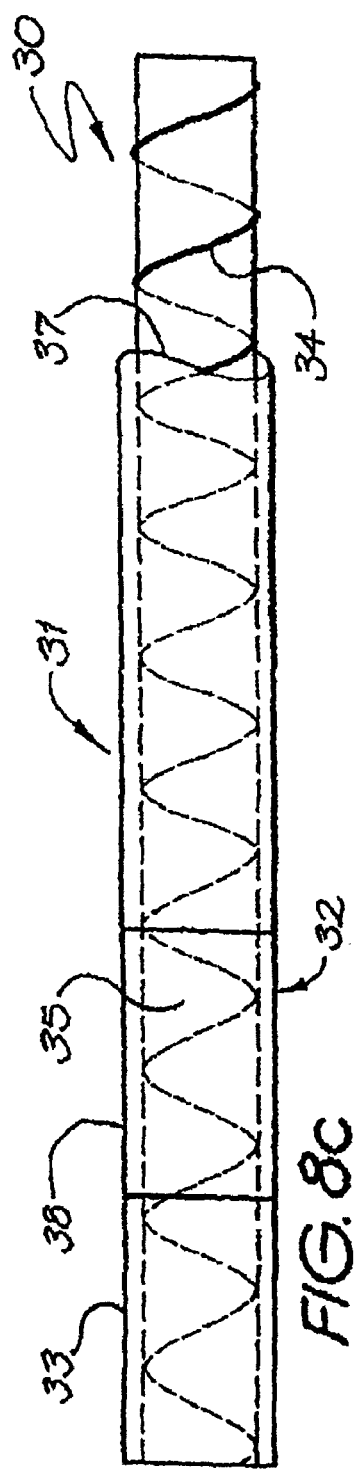

In the aspect of the invention depicted in FIGS. 8a, 8b and 8c, the invention consists of an electrically conductive member 30 including an elongate body 31. The elongate body 31 has at least one electrically conductive region 32, which comprises a polymeric material 33, together with at least one electrical conductor 34. A portion of the polymeric material 33 and a portion or all of the electrical conductor 34 are coated with an electrically conductive material 35.

The elongate body 31 comprises cylindrical first inner member 36 and a second outer member 37, the second outer member 37 substantially forming a coating around the first inner member 36. The second outer member 37 extends substantially over the entire length of the first inner member 36. The at least one electrical conductor 34 is sandwiched between the first inner member 36 and the second outer member 37.

As shown in FIG. 8b, the electrical conductor 34 is exposed. This may be achieved by a number of means including the application of heat, chemicals or lasers to remove the area of the outer member 37 covering the electrical conductor 34.

The exposed electrical conductor 34 and an area of the polymeric material 33 adjacent the electrical conductor 34 is then catalyzed and coated with the electrically conductive material 35 to form an electrode 38.

Figure 9A:
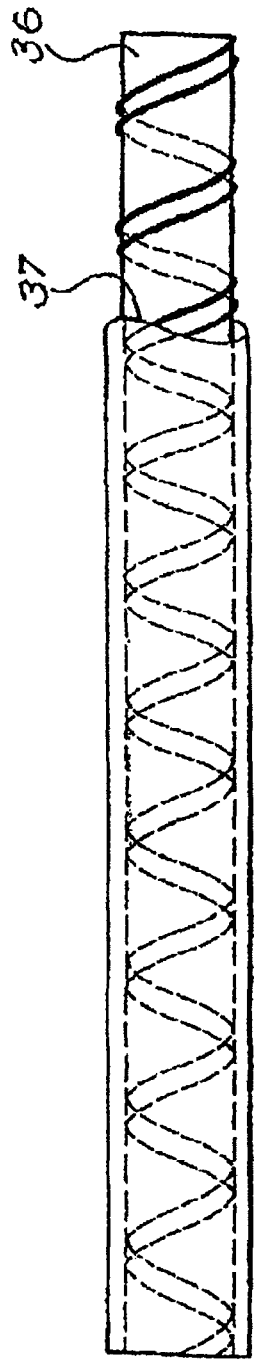
FIGS. 9a, 9b, and 9c are schematic views showing the steps of manufacture of an electrically conductive member of another embodiment of the aspect depicted in FIGS. 8a, 8b, and 8c.
Figure 9B:
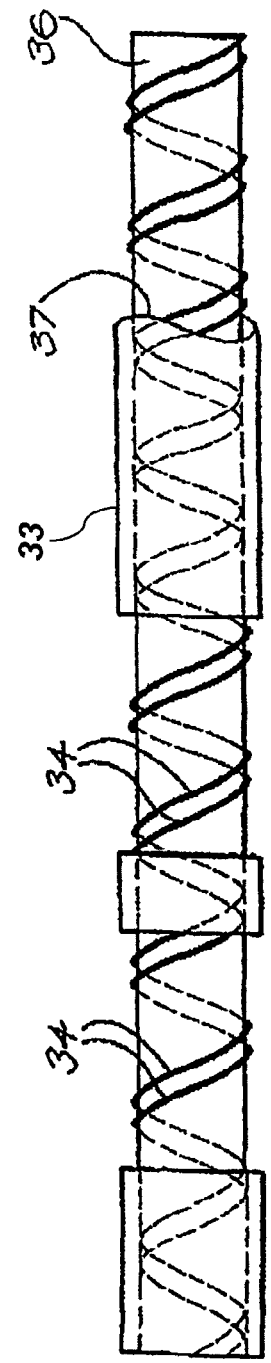
Figure 9C:
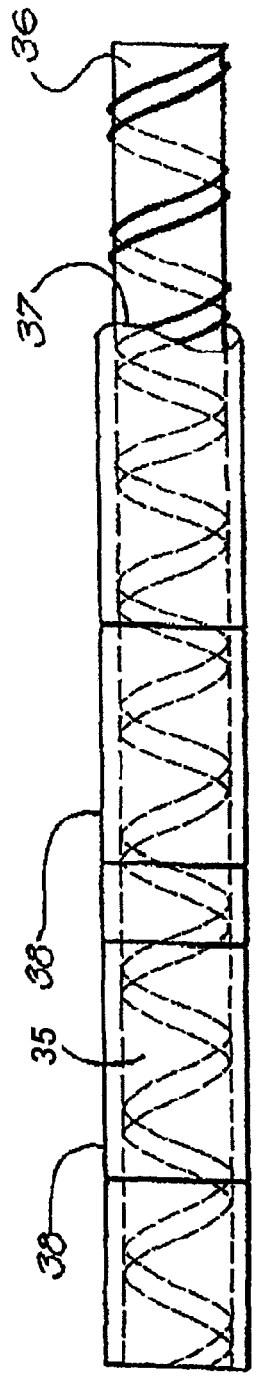

As depicted in FIGS. 9a, 9b, and 9c, two electrodes 38 may be formed by coating separate electrical conductors 34 together with an adjacent area of polymeric material 33.

Figure 10A:
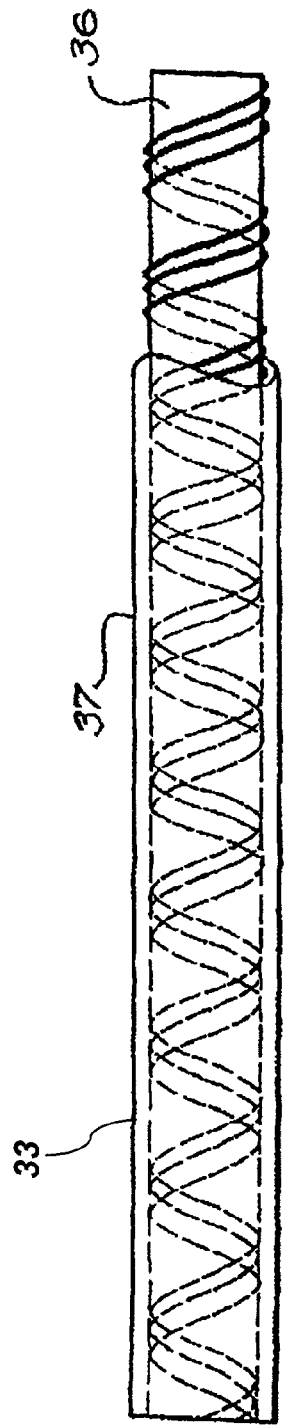
FIGS. 10a, 10b, and 10c are schematic views showing the steps of manufacture of an electrically conductive member of a further embodiment of the aspect depicted in FIGS. 8a, 8b, and 8c.
Figure 10B:
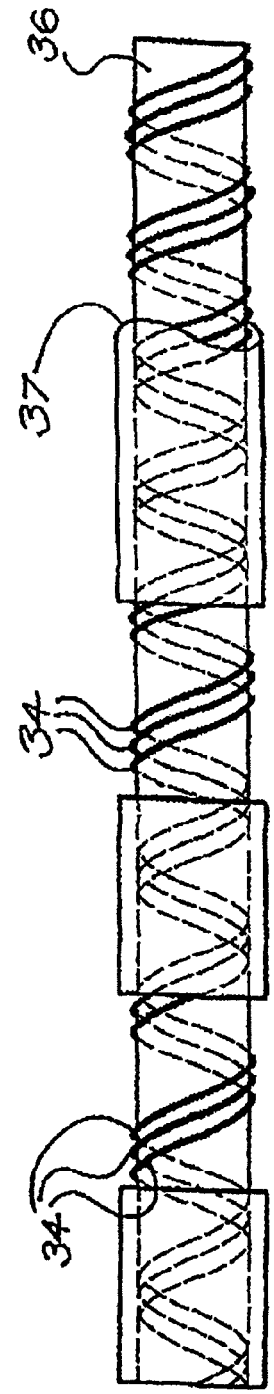
Figure 10C:
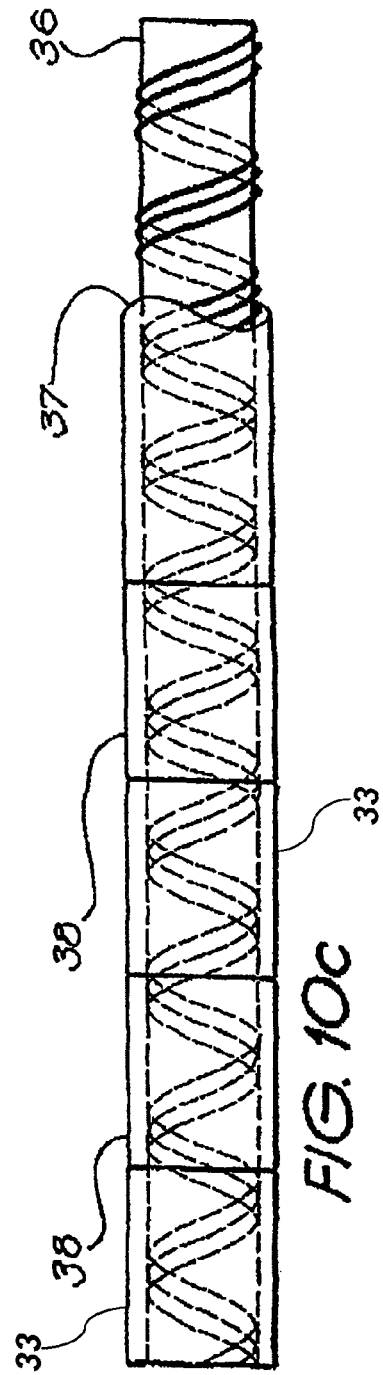

For high energy applications such as RF or microwave ablation, FIGS. 10a, 10b and 10c show how a number of electrical conductors 34, together with their adjacent polymeric material 33, may be coated with an electrically conductive material to form a single electrode 38. The electrical conductors 34 of this embodiment may be electrically connected to each other at a proximal end of each electrical conductor 34. The number of electrodes 38 formed together with the spacing between each electrode 38 may be varied.

It will be appreciated by persons skilled in the art that numerous variations and/or modifications may be made to the invention as shown in the specific embodiments without departing from the spirit or scope of the invention as broadly described. The present embodiments are, therefore, to be considered in all respects as illustrative and not restrictive.

The invention claimed is:

1. An electrical lead, including:
    an elongate body of a polymeric material, the elongate body comprising an inner member and an outer member arranged around the inner member;
    at least one electrical conductor positioned between the inner member and the outer member so that the outer member overlies the at least one electrical conductor, at least a portion of the at least one electrical conductor not being overlaid by the outer member; and
    a coating of an electrically conductive material applied to an outer surface of the elongate body at least in the region of the at least one portion of the at least one electrical conductor not overlaid by the outer member so that the coating coats at least the at least one portion of the at least one electrical conductor to define at least one electrically conductive region on the elongate body.

2. The electrical lead of claim 1, wherein the coating also coats a part of the outer member surrounding the at least one portion of the at least one electrical conductor not overlaid by the outer member.

3. The electrical lead of claim 1, wherein the elongate body is tubular and wherein the at lease one electrical conductor is contained within at least part of a wall of the tubular elongate body.

4. The electrical lead of claim 1, further including a plurality of electrical conductors wound helically about the inner member.

5. The electrical lead of claim 1, wherein the inner member and the outer member are made from a polymeric material selected from the group consisting of polyurethane and polyether block amide (PEBAX).

6. The electrical lead of claim 1, wherein the outer member is transparent so that the at least one conductor is visible through the outer member.

7. The electrical lead of claim 1, wherein the coating comprises a first layer overlain by a second layer of a biocompatible material.

8. The electrical lead of claim 7, wherein the first layer is catalyzed.

9. The electrical lead of claim 1, wherein the coating forms a band electrode extending substantially around a periphery of the elongate body.

* * * * *

UNITED STATES PATENT AND TRADEMARK OFFICE
CERTIFICATE OF CORRECTION

PATENT NO. : 8,075,969 B2
APPLICATION NO. : 12/578511
DATED : December 13, 2011
INVENTOR(S) : Neil Lawrence Anderson and Evan Ka-Loke Chong It is certified that error appears in the above-identified patent and that said Letters Patent is hereby corrected as shown below:

On the title page:
In ITEM (75) Inventors: change "Ka-loke Chong," to --Ka-Loke Chong,--

In ITEM (60) Related U.S. Application Data:
change "continuation of application" to --national phase entry under U.S.C. §371 of International Application--

Figure 2A:
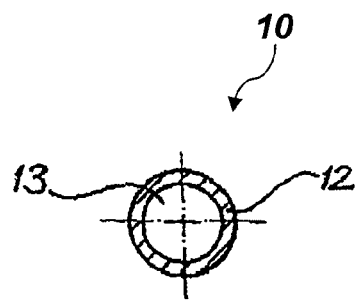
FIGS. 2a, 2b, and 2c are cross-sectional views through I-I of FIGS. 1a, 1b, and 1c respectively.

In the specification:
COLUMN 1, LINE 10, change "Internationals" to --International--
COLUMN 13, LINE 12, change "lead 10(FIG. 21)." to --lead 10 (FIG. 2*a*).--
COLUMN 13, LINE 27, change "17(FIG. 3)." to --17 (FIG. 3).--
COLUMN 13, LINE 29, change "18(FIGS. 41 and 4*b*)" to --18 (FIGS. 4*a* and 4*b*)--

In the claims:
CLAIM 3, COLUMN 15, LINE 4, change "at lease one" to --at least one--

Signed and Sealed this
Ninth Day of July, 2013

Teresa Stanek Rea
*Acting Director of the United States Patent and Trademark Office*